United States Patent [19]

Smith et al.

[11] Patent Number: 4,851,215
[45] Date of Patent: Jul. 25, 1989

[54] PANTETHINE COMPONENT FOR HAIR PERMANENT WAVING

[75] Inventors: Walter P. Smith, Long Island, N.Y.; Geoffrey R. Hawkins, Cheshire; David Yeung, Stamford, both of Conn.

[73] Assignee: Richardson-Vicks Inc., Wilton, Conn.

[21] Appl. No.: 728,205

[22] Filed: Apr. 29, 1985

[51] Int. Cl.4 .......................... A61K 7/09; A61K 7/11
[52] U.S. Cl. .......................................... 424/72; 424/71
[58] Field of Search ................................. 424/71, 70

[56] References Cited

U.S. PATENT DOCUMENTS 3,285,818 11/1966 Ohta et al. ............................ 514/616

FOREIGN PATENT DOCUMENTS 1126071 3/1962 Fed. Rep. of Germany ........ 424/72
1955823 5/1971 Fed. Rep. of Germany ........ 424/72
2749013 6/1978 Fed. Rep. of Germany ........ 424/82
0890180 2/1962 United Kingdom ................. 424/72

OTHER PUBLICATIONS

*Merck Index*, 9th Ed., Abst. 6816–6817 (1976).
Sagarin, *Cosmetics: Science & Technology*, pp. 610–620 (1957).
Chem. Abst. 97:44319t (1982).
Chem. Abst. 93:7673a (1979).

*Primary Examiner*—Douglas W. Robinson
*Attorney, Agent, or Firm*—David K. Dabbiere; Douglas C. Mohl; Jack D. Schaeffer

[57] ABSTRACT

Pantethine and pantetheine in permanent waving operations for hair to increase waving efficiency.

22 Claims, No Drawings

PANTETHINE COMPONENT FOR HAIR PERMANENT WAVING

BACKGROUND OF THE INVENTION

Permanent waving is a process whereby a reducing agent is applied to the hair structure to open the disulfide linkages of the hair which are formed by the amino acid cystine. In the conventional two-step process, hair is wound onto an appropriate mandrel, e.g., roller or rod etc., prior to and/or following reduction with a suitable reducing agent. The protein chains flow under tension to assume the imparted shape. After rinsing, an oxidizing agent is then applied to re-establish or close the disulfide linkages which, in effect, hardens the protein structure to lock it into the new position.

Permanent waving may utilize a variety of reducing agents in a first step over a wide pH range. Depending upon pH, the waving process can be carried over a wide temperature range.

An essential element of a permanent waving composition is the reducing agent. Among the reducing agents are thioglycolic acid, salts, and esters thereof; thiolactic acid and salts thereof; alkali sulfides; alkali bisulfites, cysteine, and the like. The bulk of the reducing compositions are based on thioglycolic acid, salts, or esters thereof.

The hair may be waved with thioglycolates under acid conditions, where the pH will generally range from about 5.0 to about 6.9, preferably 6.5 to about 6.9. To this end, citric, lactic, phosphoric, and weak carboxylic acids are used as common acidifying agents. Acid waves based on thioglycolates utilize elevated temperatures up to about 140° F. using heat caps, blow dryers and hair dryers. Alkali bisulfite and bisulfide waves may cover a wide pH range, from about 5.5 to 9.5, and are applied at room temperature.

Alkaline or "cold" waves are generally used at a pH in the range of 7.5 to 10.0 with ammonia, alkali carbonates and bicarbonates, ethanolamines, and alkali phosphates used as common alkalizing agents. Alkaline waves are also applied at room temperature.

The concentration of reducing agent, pH, and temperature are dictated by the hair condition, the time of processing desired, and the desired tightness of the curl.

Contact with the reducing agent may range from 10 minutes or less to 30 minutes or more. After an appropriate contact time with the reducing agent, the reducing agent is rinsed from the hair, and an oxidizing agent is applied to close the disulfide bonds and set the hair. Excess oxidizing agent is then rinsed from the hair, and the hair dried. The most common oxidizing agents are hydrogen peroxide and bromate salts. Peroxides are applied over a pH range from 2.5 to about 4.0 and bromates from a pH of about 6.0 to about 8.0. Application is at ambient or elevated temperatures.

Independent of the type of permanent wave applied, moisture is deleterious to the appearance of a permanent wave. A substantial increase in moisture content of the hair over that which existed at the time the wave was applied will tend to cause the curl to drop and become limp. By contrast, when hair of desired moisture content is exposed to low relative humidities, the hair tends to lose moisture and become frizzy.

SUMMARY OF THE INVENTION

It has now been surprisingly found that pantethine and its reduced form, pantetheine, when combined with, or used in conjunction with, or incorporated as part of the reducing agent, composition or solution applied to hair, will impart unexpected and desirable qualities to the hair when processed through a permanent waving operation. Pantethine is the common name for the known compound, N,N'-[dithiobis(ethyleneiminocarbonylethylene)]-bis(2,4-dihydroxy-3,3-dimethylbutyramide); it is freely soluble in water; it is synthesized by the formation of e peptide bond between panthenol and cysteine. Pantetheine is the common name for the reduced form of pantethine, the chemical name for which is thiobis(ethyleneiminocarbonylethylene)-bis(2,4-dihydroxy3,3-dimethylbutyramide). Both are commercially available, for example, from Chugai International Corp., New York, N.Y.

Although it is known from U.S. Pat. No. 3,285,818 that pantethine is cosmetically useful in hair tonics, surprisingly beneficial effects have now been found with its use in permanent waving operations.

Pantethine, pantetheine or mixtures thereof, hereinafter sometimes referred to as the pantethine component, is herein used in perming operations, including the acid and alkaline types, to improve waving efficiency in one or more of the following parameters, as compared to conventional waving compositions. The preferred pantethine component is pantethine itself. A most significant effect is that the pantethine component improves the curl efficacy of the permanent waving operation by decreasing the percent loss in curl retention, which is readily demonstable at elevated humidities. It also enhances penetration of the perming composition into the permed hair and, in most instances, demonstrates increased swelling of the permed hair. It also demonstrates the significant effect of lessening the chemical damage done to hair by the permanent waving operation.

DETAILED DESCRIPTION

The present invention is based on the use of the pantethine component in permanent waving solutions to improve the efficacy of the waving operation without having an adverse effect on the permed hair.

The present invention provides an improved permanent waving composition for hair which contains an effective perming amount of at least one reducing agent for hair and wherein the improvement comprises having the pantethine component in the permanent waving composition in an amount sufficient to impart to hair, permanently waved using the composition, increased waving efficiency and insufficient to have a substantial adverse affect on waving efficiency of the hair as compared to hair permanently waved using the composition in the absence of said pantethine component. By the term, "an effective perming amount of at least one reducing agent for hair", is meant an amount of reducing agent which, when applied to the hair structure in a perming operation, is sufficient to open the disulfide linkages of the hair which are formed by the amino acid cystine. The term, "increased waving efficiency," is meant to include a statistically significant increase in any of curl retention, percent penetration, percent swelling and/or a decrease in hair damage.

The compositions of this invention generally contain from about 0.005 to about 5.0 percent by weight of the pantethine component and, preferably, from about 0.01 to about 1.0 percent by weight. In alkaline perming operations, the pantethine component is incorporated into the reducing solution prior to use. In acid perming operations, it is common practice to separate the acidic reducing solution from the balancing solution until the time of use. The pantethine component may be incorporated into either solution, preferably in the balancing solution.

It is presently preferred that the reducing agent be thioglycolic acid, a salt thereof, or an ester thereof. Glycerolmonothioglycolate is presently preferred for acid compositions and ammonium thioglycolate for alkaline compositions.

The permanent hair waving process of the invention includes the steps of contacting mandrel-shaped hair with a solution of a reducing agent for hair, which includes the pantethine component, to open the disulfide linkages of the hair and the step of subsequently closing the disulfide linkages of the hair by application of an oxidizing agent to the hair to set the hair in conformity with the shape of the mandrel.

In typical use, a reducing composition, containing an effective perming amount of at least one reducing agent for hair and the pantethine component, is combined with the balance of the constituents forming a net reducing composition for application to the surface of hair in a conventional manner. After the wave is curled and rinsed, the hair is oxidized using, for example, hydrogen peroxide or a bromate salt to set the curl. Rinsing is employed following oxidation and the hair dried.

The amount of the pantethine component to be incorporated into the waving composition is an amount sufficient to impart increased waving efficiency to the permed hair without an adverse effect on the waving efficiency of the hair as determined by standard tests as compared to the same reducing composition used without the pantethine component.

With respect to acid reducing solutions, as indicated above, the pantethine component may be combined with the reducing agent, which forms one component of a two-component reducing system, the second component being termed the balancing composition. It is preferred that the balancer be an aqueous ammoniacal solution, preferably buffered. The pantethine component in combination with the reducing agent is added to the balancing solution prior to use to provide a net solution at a suitable pH for application to the hair. Alternatively, the pantethine component may first be added to the balancing composition which then is admixed with the reducing agent prior to use. For acid waves, the pH may range from 5.0 to 6.9, preferably from 6.5 to 6.9. For alkaline waves, the pH may range from 7.5 to 10.0. In the latter instance, it is not necessary to employ a balancing solution and the pantethine component may be combined with the reducing agent and suitable alkalizing agent to be applied to the hair as a one-component reducing system. As indicated, alkaline waves are applied at ambient temperatures, whereas ambient and elevated temperatures are used for acid waves with temperatures up to 140° F. conventionally employed. The hair is wound on a mandrel, e.g. rod, roller, etc., in the conventional way, and the reducing composition of the invention is applied to the hair and allowed to soften the hair structure with attendant takeup of the pantethine component. After exposure, with heating, if required, generally for about 10 to 20 minutes, the excess reducing composition is rinsed from the hair, and a suitable oxidizer, for example, hydrogen peroxide or a bromate salt is applied to reset the cystine linkages. After thorough rinsing, the hair is dried to achieve a finished curl.

As noted previously, marked beneficial results in permanent waving operations have been found upon incorporation of the pantethine component into permanent waving solutions. A most advantageous effect is that the pantethine component imparts a higher degree of waving efficiency than the same composition without the added pantethine component. This gives a tighter and more lasting curl, even upon exposure to relatively high humidity.

With respect to rate of action, the use of the pantethine component increases the rate of penetration of the reducing solution into the individual hair strands such that processing time can be reduced by up to 25 percent.

Curls permed with compositions used in accordance with the invention are less susceptible to relaxation at high humidity than curls formed when prepared with identical compositions which do not contain the pantethine component, despite the fact that more moisture is taken up by the hair. Because the hairs curled with the compositions of this invention hold more moisture at reduced humidities, as compared to hair curled without the added pantethine component, the tendency of the curl to frizz at reduced humidities is minimized.

In addition to providing higher waving efficiencies, and hair which holds a higher degree of moisture over a broad humidity range without any substantial diminution of waving efficiency, the pantethine component also imparts greater manageability, sheen and combability.

Another important feature of the subject invention is the significant decrease in hair damage found in hair permed with waving compositions containing the pantethine component as compared to this adverse effect observed in hair permed with the same waving composition without said pantethine component.

Moreover, the pantethine component has been found, for the lifetime of the prepared solutions, to be fully compatible with the reactive chemicals present in alkaline and acidic hair waving compositions.

Thus, in a process for the permanent waving of hair which includes the steps of contacting mandrel-shaped hair with a solution of reducing agent for hair to open the disulfide linkages of the hair and the step of closing the disulfide linkages of the mandrel-shaped hair by application of an oxidizing agent to the hair to set the hair in conformity with the shape of the mandrel, the instant invention provides the improvement which comprises including in the solution of said reducing agent for hair a pantethine component selected from the group consisting of pantethine, pantetheine and mixtures thereof in an amount sufficient to impart increased waving efficiency to hair permanently waved using the solution as compared to hair permanently waved using the solution in the absence of said pantethine component.

An additional feature of this invention relates to the use of the pantethine component in combination with urea. Such combined usage, when added to typical wave reducing compositions, even further increases waving efficiency than with the pantethine component alone as indicated by increased curl retention, decreased processing time and/or decreased hair damage. In general, from about 0.01 to about 5.0, and, preferably, from about 0.1 to about 1.0 percent by weight of urea is utilized in conjunction with the pantethine component.

While nowise limiting, the following examples illustrate the instant invention. In said examples, the symbol "P" signifies pantethine; the symbol "Pe" signifies Pantetheine; the symbol "U" signifies urea; and the indicated amounts are in percent by weight.

EXAMPLE 1

This example provides basic reducing formulations for both an alkaline waving operation and an acidic waving operation. These reducing formulations are used as controls in the subsequent examples. Also shown is a basic type of hydrogen peroxide oxidizing formulation used to neutralize hair permed with either the alkaline or acid reducing formulation.

| Ingredients | % w/w |
| --- | --- |
| (a) Alkaline Wave Solution (Control) | |
| Ammonium thioglycolate aqueous solution (60%) | 5.0 |
| Ammonium hydroxide aqueous solution (28%) | 4.0 |
| Water | q.s to 100.0 |
| (b) Acid Wave Solution (Control) | |
| Glycerolmonothioglycolate solution (80% GMTG, 2% thioglycolic acid and 18% glycerin) | 24.999 |
| Ammonium hydroxide aqueous solution (28%) | 0.001 |
| Water | 75.000 |
| (c) Neutralizer | |
| Hydrogen peroxide solution (50%) | 4.10 |
| Phenacetin | 0.04 |
| Water | 95.0 |
| Phosphoric acid (85%) | q.s. to pH 3.0-3.5 |

EXAMPLE 2

Improving Curl Efficacy of a Perm

Virgin hair swatches, approximately 2 grams in weight, are bound together at one end and trimmed to 7 inches. After spraying with water to moisten, the hair swatch is wound tightly around a 1/2 inch diameter perming rod. The moistened hair swatch is permed in the waving solution for 20 minutes, and then thoroughly rinsed with water. Then the swatch is neutralized with the neutralizer of Example 1 for 5 minutes and rinsed again. The hair swatch is blown dry with low heat (40°-50° C.) until thoroughly dry. After drying, the hair swatch is carefully unwound from the perming rod and hung vertically from the bound end. The initial length of the curl is measured before exposure in the humidity chamber and this measurement serves as the control basis against which the curl efficiency of the tested perm is determined. The hair swatches are then placed in a humidity chamber set at 90% relative humidity (RH) and 37° C. Relaxation of the swatches is measured after 60 minutes in the humidity chamber. The swatches that undergo the least amount of relaxation at elevated humidity demonstrate the most effective perms. The "percent loss in curl retention" is determined by the formula:

$$\frac{\text{length at given humidity for given time} - \text{initial length}}{\text{initial length}} \times 100$$

| Treatment | Waving Efficiency | | | | |
| --- | --- | --- | --- | --- | --- |
| | Initial Curl Length (cm) | Curl Length at 60' (cm) | Change in Curl Length (cm) | % Loss in Curl Retention | % Improvement over Alkaline Control |
| Alkaline Control | 3.7 | 11.5 | 7.8 | 210.8 | 0 by definition |
| +0.01% P | 4.5 | 8.3 | 3.8 | 84.4 | 60.0% |
| +1.0% P | 5.6 | 9.1 | 3.5 | 62.5 | 70.4% |
| | | | | | % Improvement over Acid Control |
| Acid Control | 3.8 | 9.4 | 5.6 | 147.4 | 0 by definition |
| +0.01% P | 5.3 | 12.0 | 6.7 | 126.4 | 14.2% |
| +1.0% P | 4.4 | 10.2 | 5.8 | 131.8 | 10.6% |

Improved results in waving efficiency are also obtained upon addition of 0.01 and 1.0 percent by weight of pantetheine to the alkaline and acid waving solution controls of this Example 2.

EXAMPLE 3

Pantethine Component and Urea

This example demonstrates the combined use of the pantethine component and urea to further improve waving efficiency.

| Treatment | Waving Efficiency | | | | |
| --- | --- | --- | --- | --- | --- |
| | Initial Curl Length (cm) | Curl Length at 60' (cm) | Change in Curl Length (cm) | % Loss in Curl Retention | % Improvement over Acid Control |
| Acid Control | 3.8 | 9.4 | 5.6 | 147.4 | 0 by definition |
| +0.01% P | 5.3 | 12.0 | 6.7 | 126.4 | 14.2% |
| +0.01% P +0.01% U | 4.9 | 10.2 | 5.3 | 108.2 | 26.6% |
| +1.0% P | 4.4 | 10.2 | 5.8 | 131.8 | 10.6% |
| +1.0% P +0.01% U | 4.4 | 9.5 | 5.1 | 115.9 | 21.4% |
| | | | | | % Improvement over Alkaline Control |
| Alkaline Control | 2.1 | 8.0 | 5.9 | 281.0 | 0 by definition |
| +0.2% Pe +0.5% U | 2.1 | 6.7 | 4.6 | 219.0 | 22.1% |

EXAMPLE 4

Salon Test

This example demonstrates the usefulness of the subject compositions in penetrating hair and in decreasing the amount of time required for perming operations under actual salon conditions. The penetration of active ingredients in perms is tested on consumers in the salon utilizing a half-head method where the hair is shampooed, divided from the nape of the neck to the center of the forehead and wound on to the perming rods. A perm solution without the pantethine component is used to perm one side and a perm solution with the pantethine component is used to perm the other side. Each solution is applied to thoroughly wet the hair. In evaluating acid waves, the procedure is modified by adding heat (40°-50° C.) with a hair dryer. Both sides of the head are processed simultaneously; generally about 5-15 minutes depending on hair type and porosity. Processing takes place until an S-curl is observed or until the cosmetologist feels the perm has processed adequately. The time required for processing to be complete is recorded. Since penetration and processing time are dependent on each other, the side which is processed faster is also the side where the active ingredients penetrated faster. The hair is then rinsed for about 5 minutes using lukewarm water followed by neutralization with hydrogen peroxide solution for about 5 minutes. The hair is then rinsed again with lukewarm water. The rods are now removed and the hair appropriately styled.

A. Alkaline Wave: Five individuals with normal hair were evaluated for perm processing speed using an alkaline wave with and without pantethine. The alkaline wave containing pantethine had an average processing time of 10 minutes. The alkaline wave without pantethine required 12-13 minutes. Thus, the addition of pantethine increased processing speed and concommitant penetration of perm actives by about 20%.

B. Acid wave: Five individuals with tinted or fine hair were evaluated for perm processing speed utilizing an acid wave with and without pantethine. The acid wave containing pantethine had an average processing time of 10 minutes. The acid wave without pantethine required 12-13 minutes. Again, the addition of pantethine increased processing speed and penetration of perm actives by about 20%.

EXAMPLE 5

Determination of Perm Penetration by Iodine Staining

This example demonstrates the increased penetration of perm actives by the inclusion of the pantethine component according to the conventional iodine staining test for measuring percent penetration and percent swelling (see, for example, Example 21 of U.S. Pat. No. 4,301,820).

Virgin blond hair swatches, approximately 2 grams in weight, are soaked in 0.1N Standarized Iodine Solution (Anachemia Chemicals, Inc., Champlain, N.Y.) for 24 hours. A single iodine stained hair strand is placed on a microscopic slide. Using 100X magnification, the initial fiber diameter ($D_O$) is measured with a micrometer. Approximately 5 drops of the perm solution to be tested is applied to the hair on the slide and covered with a cover slip. When evaluating acid waves, the procedure is modified by heating the slide (40°-50° C.) with a blow-dryer during the 20 minute penetration period. The perm solution penetrates the iodine-dyed hair and the reducing agent in the perm solution reacts with the iodine turning the penetrated portion of the dyed hair colorless. The iodine boundary diameter ($D_B$) is determined 20 minutes after application of the perm solution. The percent penetration is determined by the equation:

$$\% \text{ Penetration} = \frac{D_O - D_B}{D_O} \times 100$$

In addition, the percent swelling of the hair fiber which occurs with application of perm solution is evaluated. The total fiber diameter of the hair strand ($D_T$) is measured 20 minutes after application of the perm solution. Percent swelling is determined by the equation:

$$\% \text{ Swelling} = \frac{D_T - D_O}{D_O} \times 100$$

Change in Penetration of Perm Actives and Hair Swelling

| Treatment | $D_O$ | $D_B$ | $D_T$ | % Penetration | % Increase in Penetration | % Swelling | % Increase in Swelling |
|---|---|---|---|---|---|---|---|
| | (microns) | | | | | | |
| Alkaline Control | 70 | 45 | 75 | 35.7 | 0 by definition | 7.1 | 0 by definition |
| +0.01% P | 65 | 36 | 80 | 44.6 | 24.9% | 23.1 | 225.4 |
| +1.0% P | 60 | 35 | 65 | 41.7 | 16.8% | 8.3 | 16.9 |
| Acid Control | 72 | 50 | 80 | 30.6 | 0 by definition | 11.1 | 0 by definition |
| +0.01% P | 68 | 40 | 73 | 41.2 | 34.6% | 7.4 | −33.3 |
| +1.0% P | 57 | 28 | 70 | 50.8 | 66.0% | 22.8 | 105.4 |

EXAMPLE 6

Pantethine Component and Urea

This example demonstrates the enhancement in percent penetration and percent swelling resulting from the combined use of the pantethine component and urea in the subject compositions.

| Treatment | $D_O$ | $D_B$ | $D_T$ | % Penetration | % Increase in Penetration | % Swelling | % Increase in Swelling |
|---|---|---|---|---|---|---|---|
| | (microns) | | | | | | |
| Alkaline Control | 70 | 45 | 75 | 35.7 | 0 by definition | 7.1 | 0 by definition |
| +1.0% P | 60 | 35 | 65 | 41.2 | 16.8% | 8.3 | 16.9 |
| +1.0% P +5.0% U | 70 | 30 | 80 | 57.1 | 59.9% | 14.3 | 101.4 |

EXAMPLE 7

Assessment of Hair Damage

Perming hair results in chemical damage of hair since disulfide bonds are broken by the reducing operation. The subsequent use of neutralizer does not reform all the broken bonds and, consequently, the hair to a certain extent remains damaged. Yield slope analysis illustrates the technique used to analyze hair strength which correlates with disulfide bond breakage. Thus, the less damaging the perm is, the less change in yield slope will be observed after perming.

Virgin hair, approximately 2 grams in weight and at least 25 cm long is bound together at one end. The swatches are then soaked in the appropriate perm solutions for 20 minutes. After thorough rinsing with water to remove excess perm solution, the hair bundles are neutralized for 5 minutes and rinsed again. Swatches are air-dried until thoroughly dry, generally for at least 12 hours, at ambient temperature. utilizing a tensile strength tester (Instron Model #1122, manufactured by the Instron Corp., Canton, MA), a single strand of hair is positioned between the two clamps of the tester at a standardized distance of 23 cm. With the instrument set at a crosshead speed of 100 mm/minute and a chart speed of 200 mm/minute, at least 20 single hair strands from each group are extended with a 20 g load setting. The slope of the yield region which correlates with covalent and disulfide bond breakage (i.e. overall hair damage) is measured for each hair. For each group of virgin hair, the mean yield slope for the 20 single hair strand measurements is calculated. The yield slope of unpermed virgin hair represents totally undamaged hair (Control A). The mean yield slope of virgin hair permed with the reducing solution to be tested minus the pantethine component represents maximally damaged hair due to the perming operation (Control B). The mean yield slope of virgin hair permed with the same reducing solution plus the pantethine component is then measured (Perm C) and the percent reduction in hair damage is determined according to the formula:

$$\% \text{ Reduction in Hair Damage} = \frac{\text{Perm } C - \text{Control } B}{\text{Control } A - \text{Control } B}$$

| Treatment | Yield Slope | % Reduction in Hair Damage |
| --- | --- | --- |
| A. Damage Reduction With Alkaline Waves (pH 10) | | |
| Alkaline Control | .257 | 0.0 |
| +0.01% P | .298 | 43.2 |
| +0.01% P + 0.01% U | .321 | 67.4 |
| +0.01% P + 5.0% U | .322 | 68.4 |
| +1.0% P | .306 | 51.6 |
| +1.0% P + 0.01% U | .341 | 88.4 |
| +1.0% P + 5.0% U | .346 | 93.7 |
| B. Damage Reduction With Acid Waves (pH 3) | | |
| Acid Control | .246 | 0.0 |
| +0.01% P | .296 | 47.2 |
| +0.01% P + 0.01% U | .319 | 68.9 |
| +0.01% P + 5.0% U | .319 | 68.9 |
| +1.0% P | .319 | 68.9 |
| +1.0% P + 0.01% U | .341 | 89.6 |
| +1.0% P + 5.0% U | .341 | 89.6 |

| Treatment | Yield Slope | % Reduction in Hair Damage |
| --- | --- | --- |
| A. Damage Reduction With Alkaline Waves (pH 10) | | |
| Alkaline Control | .257 | 0.0 |
| +0.01% P | .298 | 43.2 |
| +0.01% P + 0.01% U | .321 | 67.4 |
| +0.01% P + 5.0% U | .322 | 68.4 |
| +1.0% P | .306 | 51.6 |
| +1.0% P + 0.01% U | .341 | 88.4 |
| +1.0% P + 5.0% U | .346 | 93.7 |
| B. Damage Reduction With Acid Waves (pH 3) | | |
| Acid Control | .246 | 0.0 |
| +0.01% P | .296 | 47.2 |
| +0.01% P + 0.01% U | .319 | 68.9 |
| +0.01% P + 5.0% U | .319 | 68.9 |
| +1.0% P | .319 | 68.9 |
| +1.0% P + 0.01% U | .341 | 89.6 |
| +1.0% P + 5.0% U | .341 | 89.6 |

EXAMPLE 8

Bisulfite Perm

The following bisulfite waving formation (pH 7.0) is used as a Control in testing the waving efficiency.

| Ingredients | % w/w |
| --- | --- |
| Sodium bisulfite | 8.0 |
| Ammonium hydroxide (28%) | 0.2 |
| Water | 91.8 |
| | 100.0 |

| Treatment | Waving Efficiency | | | | |
| --- | --- | --- | --- | --- | --- |
| | Initial Curl Length (cm) | Curl Length at 60' (cm) | Change in Curl Length (cm) | % Loss in Curl Retention | % Improvement over Bisulfite Control |
| Bisulfite Control | 4.2 | 9.3 | 5.1 | 121.4 | 0 by definition |
| +0.2% P +2.0% U | 4.5 | 9.3 | 4.8 | 106.7 | 12.1% |

EXAMPLE 9

Mixture of Pantethine and Pantetheine

| Treatment | Waving Efficiency | | | | |
| --- | --- | --- | --- | --- | --- |
| | Initial Curl Length (cm) | Curl Length at 60' (cm) | Change in Curl Length (cm) | % Loss in Curl Retention | % Improvement over Alkaline Control |
| Alkaline Control | 7.5 | 12.5 | 5.0 | 66.0 | 0 by definition |
| +0.2% P +2.0% Pe | 7.0 | 9.5 | 2.5 | 35.7 | 46.2% |

We claim:

1. In a permanent waving composition for hair which contains an effective perming amount of at least one reducing agent for hair and wherein the improvement comprises having in said composition a pantethine component selected from the group consisting of pantethine, pantetheine and mixtures thereof in an amount sufficient to impart increased waving efficiency to hair permanently waved using the composition as compared to hair permanently waved using the composition in the absence of said pantethine component.

2. In a permanent waving composition for hair which contains an effective perming amount of at least one reducing agent for hair and wherein the improvement comprises having in said composition from about 0.005 to about 5.0 percent by weight of a pantethine component selected from the group consisting of pantethine, pantetheine and mixtures thereof.

3. A composition as claimed in claim 2 wherein said pantethine component is pantethine.

4. A composition as claimed in claim 2 also having therein from about 0.01 to about 5.0 percent by weight of urea.

5. A composition as claimed in claim 2 of the alkaline type wherein said reducing agent is ammonium thioglycolate.

6. A composition as claimed in claim 2 of the acid type wherein said reducing agent is glycerolmonothioglycolate.

7. In a permanent waving composition for hair which contains an effective perming amount of at least one reducing agent for hair and wherein the improvement comprises having in said composition from about 0.01 to about 1.0 percent by weight of a pantethine component selected from the group consisting of pantethine, pantetheine and mixtures thereof.

8. A composition as claimed in claim 7 wherein said pantethine component is pantethine.

9. A composition as claimed in claim 8 also having therein from about 0.1 to about 1.0 percent by weight of urea.

10. An alkaline wave perming composition of pH 7.5–10 as claimed in claim 8 wherein said reducing agent is ammonium thioglycolate.

11. An acid wave perming composition of pH 5.0–6.9 as claimed in claim 8 wherein said reducing agent is glycerolmonothioglycolate.

12. In a process for the permanent waving of hair which includes the steps of contacting mandrel-shaped hair with a solution of reducing agent for hair to open the disulfide linkages of the hair and the step of closing the disulfide linkages of the mandrel-shaped hair by application of an oxidizing agent to the hair to set the hair in conformity with the shape of the mandrel, the improvement which comprises including in the solution of said reducing agent for hair a pantethine component selected from the group consisting of pantethine, pantetheine and mixtures thereof in an amount sufficient to impart increased waving efficiency to hair permanently waved using the solution as compared to hair permanently waved using the solution in the absence of said pantethine component.

13. In a process for the permanent waving of hair which includes the steps of contacting mandrel-shaped hair with a solution of reducing agent for hair to open the disulfide linkages of the hair and the step of closing the disulfide linkages of the mandrel-shaped hair by application of an oxidizing agent to the hair to set the hair in conformity with the shape of the mandrel, the improvement which comprises including in the solution of said reducing agent for hair from about 0.005 to about 5.0 percent by weight of a pantethine component selected from the group consisting of pantethine, pantetheine and mixtures thereof.

14. A process as claimed in claim 13 wherein said pantethine component is pantethine.

15. A process as claimed in claim 13 wherein said reducing agent solution also has therein from about 0.01 to about 5.0 percent by weight of urea.

16. A process as claimed in claim 13 wherein and said reducing agent is alkaline with pH 7.5–10 said reducing agent is ammonium thioglycolate.

17. A process as claimed in claim 13 wherein said reducing agent solution is acidic with pH 5.0–6.9 and said reducing agent is glycerolmonothioglycolate.

18. In a process for the permanent waving of hair which includes the steps of contacting mandrel-shaped hair with a solution of reducing agent for hair to open the disulfide linkages of the hair and the step of closing the disulfide linkages of the mandrel-shaped hair by application of an oxidizing agent to the hair to set the hair in conformity with the shape of the mandrel, the improvement which comprises including in the solution of said reducing agent for hair from about 0.01 to about 1.0 percent by weight of a pantethine component selected from the group consisting of pantethine, pantetheine and mixtures thereof.

19. A process as claimed in claim 18 wherein said pantethine component is pantethine.

20. A process as claimed in claim 18 wherein said reducing agent solution also has therein from about 0.1 to about 1.0 percent by weight of urea.

21. A process as claimed in claim 18 wherein said reducing agent solution is of the alkaline type and said reducing agent is ammonium thioglycolate.

22. A process as claimed in claim 18 wherein said reducing agent solution is of the acid type and said reducing agent is glycerolmonothioglycolate.

* * * * *